(12) United States Patent
Ghosh et al.

(10) Patent No.: US 7,196,237 B2
(45) Date of Patent: Mar. 27, 2007

(54) METHOD OF PREPARING AN ALKYL AROMATIC PRODUCT

(75) Inventors: Ashim Kumar Ghosh, Houston, TX (US); Pamela Harvey, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 153 days.

(21) Appl. No.: 11/134,567

(22) Filed: May 20, 2005

(65) Prior Publication Data

US 2005/0209494 A1 Sep. 22, 2005

Related U.S. Application Data

(62) Division of application No. 10/790,948, filed on Mar. 2, 2004, now Pat. No. 6,943,131.

(51) Int. Cl.
*C07C 2/66* (2006.01)
*C07C 2/70* (2006.01)

(52) U.S. Cl. ........................... 585/467; 585/446
(58) Field of Classification Search ................ 585/446, 585/467
See application file for complete search history.

(56) References Cited

U.S. PATENT DOCUMENTS

| | | | |
|---|---|---|---|
| 3,702,886 A | 11/1972 | Argauer et al. |
| 3,965,207 A | 6/1976 | Weinstein |
| 4,278,827 A | 7/1981 | Chu et al. |
| 4,548,914 A | 10/1985 | Chu |
| 4,590,321 A | 5/1986 | Chu |
| 4,623,530 A | 11/1986 | Cullo et al. |
| 4,623,533 A | 11/1986 | Young |
| 4,638,106 A | 1/1987 | Pieters et al. |
| 4,665,251 A | 5/1987 | Chu |
| 4,670,616 A | 6/1987 | De Simone et al. |
| 4,673,767 A | 6/1987 | Nimry et al. |
| 4,694,114 A | 9/1987 | Chu et al. |
| 4,695,666 A | 9/1987 | Chao et al. |
| 4,695,667 A | 9/1987 | Sumitani et al. |
| 4,704,495 A | 11/1987 | Dessau |
| 4,716,135 A | 12/1987 | Chen |
| 4,721,827 A | 1/1988 | Cullo et al. |
| 4,727,209 A | 2/1988 | Chao |
| 4,746,763 A | 5/1988 | Kocal |
| 4,758,328 A | 7/1988 | Young |
| 4,761,513 A | 8/1988 | Steacy |
| 4,847,223 A | 7/1989 | Le Van Mao et al. |
| 4,861,930 A | 8/1989 | Cottrell et al. |
| 4,873,067 A | 10/1989 | Valyocsik et al. |
| 4,891,197 A | 1/1990 | Derouane et al. |
| 4,891,467 A | 1/1990 | Sikkenga |
| 4,902,406 A | 2/1990 | Valyocsik |
| 4,912,073 A | 3/1990 | Chu |
| 4,914,067 A | 4/1990 | Pellet et al. |
| 4,935,574 A | 6/1990 | D'Amore et al. |
| 4,962,255 A | 10/1990 | Fraenkel et al. |
| 4,973,781 A | 11/1990 | Valyocsik et al. |
| 5,041,402 A | 8/1991 | Casci et al. |
| 5,043,502 A | 8/1991 | Martindale et al. |
| 5,047,141 A | 9/1991 | Chu |
| 5,068,483 A | 11/1991 | Barthomeuf et al. |
| 5,094,995 A | 3/1992 | Butt et al. |
| 5,105,047 A | 4/1992 | Waller |
| 5,108,579 A | 4/1992 | Casci |
| 5,110,776 A | 5/1992 | Chitnis et al. |
| 5,124,299 A | 6/1992 | Waller |
| 5,171,921 A | 12/1992 | Gaffney et al. |
| 5,173,461 A | 12/1992 | Absil et al. |
| 5,178,748 A | 1/1993 | Casci et al. |
| 5,210,356 A | 5/1993 | Shamshoum et al. |
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |

(Continued)

OTHER PUBLICATIONS

Kaeding, W.W., et al., Selective Alkylation of Toluene to Produce para-Xylene, Journal of Catalysis, 1981, pp. 159-174, vol. 67.

(Continued)

*Primary Examiner*—Elizabeth D. Wood
(74) *Attorney, Agent, or Firm*—Grady K. Bergen; Jim D. Wheelington; Griggs Bergen LLP

(57) ABSTRACT

A method of modifying a zeolite catalyst to increase selectivity of the catalyst is achieved by dissolving alumina in a phosphorus-containing acid solution, and treating the zeolite catalyst with the dissolved alumina solution. A method of preparing an aromatic product, such as a xylene product, is also achieved by contacting the modified zeolite catalyst with an aromatic hydrocarbon, such as toluene, and an alkylating agent, such as methanol, under reaction conditions suitable for aromatic alkylation. For xylene products the aromatic hydrocarbon may be toluene and the reaction conditions may be suitable for at least one of toluene methylation and transalkylation.

15 Claims, 3 Drawing Sheets

U.S. PATENT DOCUMENTS

| | | |
|---|---|---|
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Berduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,589,901 B2 | 7/2003 | Yamamoto et al. |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |

OTHER PUBLICATIONS

Niwa, M., et al., Fine Control of the Pore-Opening Size of Zeolite ZSM-5 by chemical Vapor Deposition of Silicon Methoxide, J. Phys. Chem, 1986, pp. 6233-6237, vol. 90.

METHOD OF PREPARING AN ALKYL AROMATIC PRODUCT

This application is a division of U.S. patent application Ser. No. 10/790,948, now U.S. Pat. Ser. No. 6,943,131 entitled "Selective Catalyst Modification," filed Mar. 2, 2004, which is herein incorporated by reference in its entirety.

TECHNICAL FIELD

The invention relates generally to the alkylation of aromatic compounds and catalysts used for such reactions.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

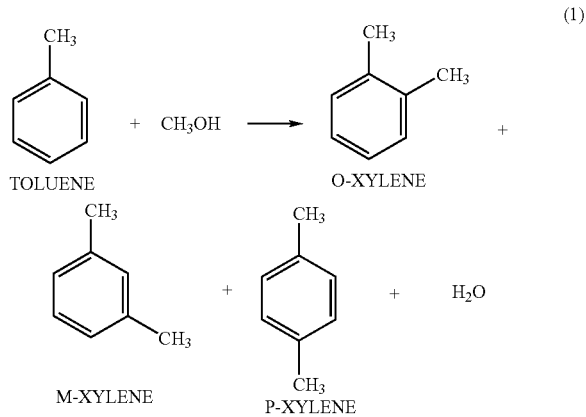

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

In Kaeding, et al, *Selective Alkylation of Toluene with Methanol to Produce para-Xylene*, Journal of Catalysis, Vol. 67, pp. 159–174 (1981), a procedure of making a ZSM-5 catalyst by incorporating 5% phosphorus was described in which the catalyst was impregnated with a solution of diphenylphosphinous acid in toluene. The ZSM-5 catalyst thus modified showed toluene methylation activity with 84–90% para isomer in the xylene product. In another procedure, a catalyst was modified by incorporating 8.51% phosphorus from an aqueous phosphoric acid reagent. The catalyst showed p-xylene selectivity as high as 97%, however, the catalyst showed a decreasing activity within hours due to coke deposition.

Unfortunately, there are a number of technical hurdles for toluene methylation to be commercially successful. These include fast catalyst deactivation, low methanol selectivity, and so on. Most, if not all, of the catalysts used for toluene methylation show fast catalyst deactivation. Typically, toluene conversion declines with time on stream due to rapid coke formation on the catalyst. The catalyst deactivation is one of the most difficult technical hurdles to overcome for commercial use of toluene methylation.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
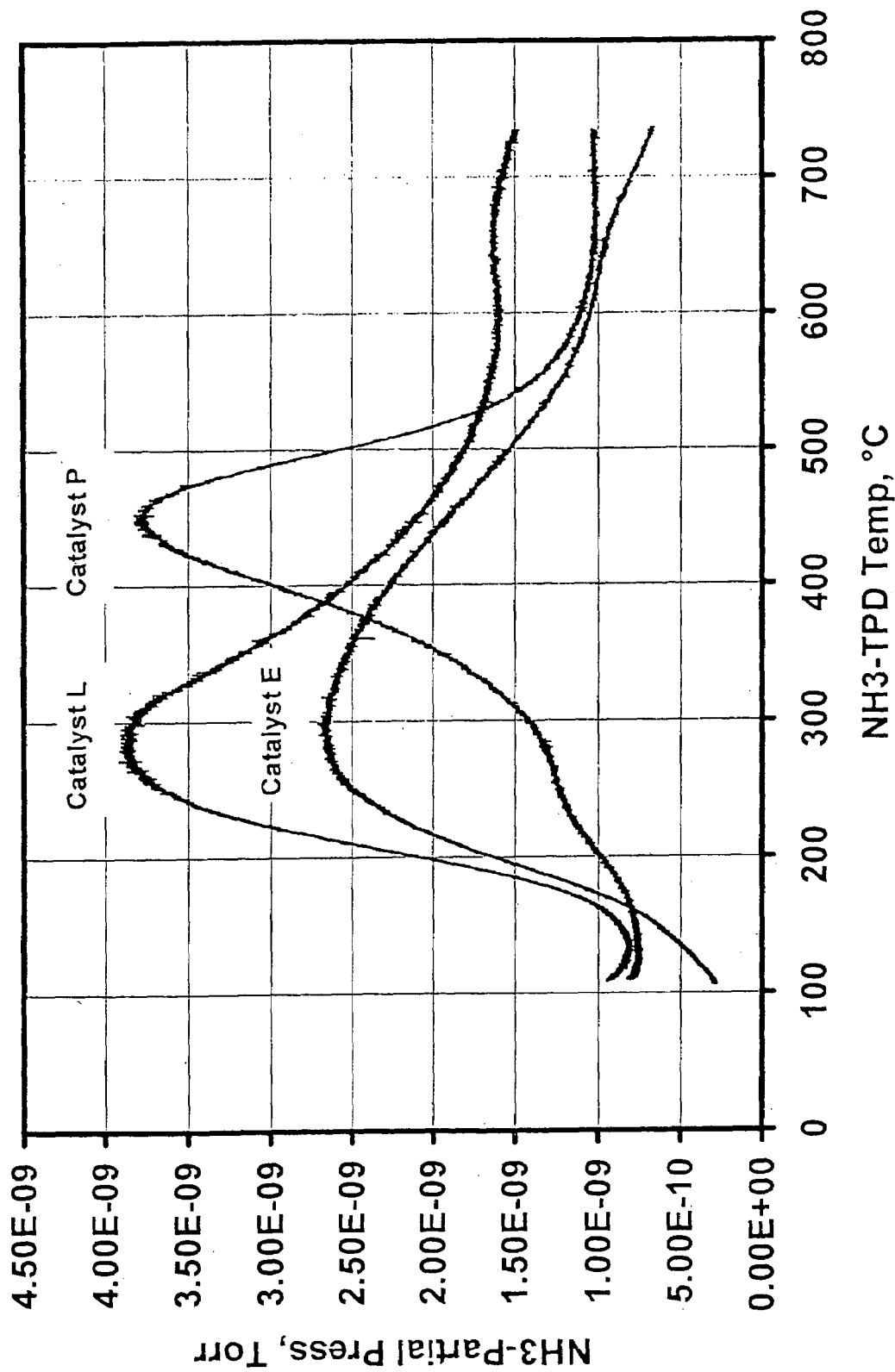
FIG. 1 is a plot of $NH_3$-TPD for alumina-PA modified ZSM-5 (E), PA modified ZSM-5 (L), and non-modified ZSM-5 (P) catalysts.

The modification of ZSM-5-type zeolite catalysts with phosphoric acid (PA) has been shown to yield significantly greater amounts of p-xylene than the thermodynamic equilibrium value in toluene methylation with unmodified catalysts. It has been found, however, that increased selectivity for para-xylene beyond that achieved from phosphoric acid-only modified zeolites, given the same quantity of phosphoric acid usage, can be achieved by incorporating dissolved or "digested" alumina into such catalysts.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in any limiting sense. The ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of from 25 to 1000 prior to modification, more particularly a silica/alumina molar ratio of from about 30 to about 300 prior to modification.

Although specific reference has been made to ZSM-5-type zeolites for use in toluene methylation, for which the invention has particular application, the modification discussed herein may have application to other zeolites with pore diameters ranging from 5.0 Å to 7.0 Å, such as mordenite, omega, etc. Additionally, specific reference is made to the use of the modified catalyst in toluene methylation, for which the modified zeolite is particularly well suited. It will be apparent to those skilled in the art, however, that the catalyst may have application for use in other types of reactions, such as transalkylation and other aromatic alkylation reactions. In particular, the catalyst of the invention may have application to such reactions to provide increased selectivity for para-isomer in mixed dialkylated aromatic products.

As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for total xylenes may be expressed as:

$$\text{Mole \% Total Xylene Selectivity} = [X_{tx}/(T_i - T_o)] \times 100 \quad (3)$$

where, $X_{tx}$ is the number of moles of total (o-, m- or p-) xylenes in the product. As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.

The zeolite may be modified by treating the zeolite with alumina that has been pre-dissolved in a phosphorus (P) containing inorganic acid, such as phosphoric acid ($H_3PO_4$, pKa=2.12 for step 1) or phosphorus acid ($H_3PO_3$, pKa=2.00 for step 1). Although specific mention of phosphoric acid is made in the description that follows, it should be apparent that other phosphorus-containing acids could be used instead. The alumina, which is initially in a solid form, is dissolved in the acid solution. The phosphoric acid solution may be of sufficient concentration and quantity to dissolve all or substantially all of the alumina, which may be evident when the solution turns clear. Any remaining or undissolved alumina may be filtered or otherwise removed from the solution prior to use in modifying the zeolite catalyst, if necessary.

In dissolving the alumina, the phosphoric acid may be used in excess amounts, as is discussed further on. Examples of suitable amounts of alumina may be from about 0.005 g to about 0.10 g alumina per gram of zeolite powder. Suitable amounts of the phosphoric acid may be from about 0.05 g or more to about 0.5 g per gram of zeolite powder. The acid may be in a concentrated liquid form of at least 50% acid by weight of aqueous solution, such as 85% acid by weight aqueous solution.

To facilitate dissolving the alumina, it can be first added to water and stirred while heated to an elevated temperature. The phosphoric acid may then be added to the alumina. An example of a suitable temperature is from about 70 to about 100° C. The dissolved alumina solution may contain an excess amount or residual phosphoric acid.

Prior to adding the alumina-containing phosphoric acid solution, the zeolite powder may be combined with water to make an aqueous slurry or suspension. The slurry may be heated and stirred to facilitate catalyst preparation. An example of a suitable temperature range for the zeolite slurry is from about 70 to about 100° C. The dissolved alumina may then be combined with the zeolite slurry. Alternatively, the dissolved alumina may be added to dry zeolite powder to form zeolite slurry.

Excess or residual phosphoric acid remaining in the dissolved alumina solution may facilitate modification of the zeolite to provide shape selective properties. Alternatively, additional phosphoric acid may be added to the slurry to modify or further facilitate modification of the zeolite to provide shape selective properties. In the case of ZSM-5-type zeolites, these catalysts can be modified to increase selectivity for p-xylene in toluene methylation reactions through modification of the zeolite with phosphoric acid. The incorporation of the alumina from the dissolved alumina solution, however, has been shown to further increase the selectivity of the zeolite beyond that achieved through modification solely with phosphoric acid, as is illustrated by the examples discussed further on.

The zeolite slurry, which now contains the dissolved alumina/acid solution, may then be heated until all liquids are evaporated. An example of a suitable temperature range is from 70° C. to 100° C. The slurry may also be stirred or agitated during this step to ensure uniform treatment.

The alumina-PA-modified zeolite catalyst may be used unbound or be bound with a binder. Examples of suitable binders include such materials as alumina, clay, and silica. Those techniques used for preparing the bound catalyst are well known in the art. The catalyst, bound or unbound, may be calcined at a temperature between 400° C. and 570° C. in an environment containing oxygen, typically air.

The modified catalyst may be contacted with an appropriate feed under alkylation reaction conditions to carry out aromatic alkylation. Examples of alkylation reactions for which the invention has application include toluene alkylation with an alkylating agent such as methanol. Other alkylation reactions may include transalkylation, such as gas phase toluene disproportionation in the presence of hydrogen to produce benzene and mixed xylenes.

The reactor pressure for toluene methylation or other aromatic alkylation may vary, but typically ranges from about 10 to about 1000 psig.

The reaction may be carried in a variety of different reactors that are commonly used for carrying out aromatic alkylation reactions. Single or multi reactors in series and/or parallel are suitable for carrying out the toluene methylation or other aromatic alkylation reactions.

In particular, the modified catalyst is useful in toluene methylation for preparing a xylene product from a feed of toluene and methanol that has increased selectivity for p-xylene. In such reactions, water may be introduced with the feed in an amount of at least 0.1 moles water per mole of toluene/methanol feed, as described in U.S. patent application Ser. No. 10/675,780, filed Sep. 30, 2003, which is herein incorporated by reference. A hydrogen cofeed is also used. The hydrogen may be used in an amount of at least 1.0 mole per mole of toluene+methanol feed.

When ZSM-5-type zeolite catalysts modified in accordance with the invention are used in toluene methylation, a xylene product having a p-xylene content of 80%, 85%, 90% or 95% or more by total moles of xylene may be obtained.

The following examples further illustrate the invention.

EXAMPLES

Catalyst Preparation

Catalysts A–H

To form each catalyst, a slurry of $NH_4$-ZSM-5 zeolite powder having a $SiO_2/Al_2O_3$ mole ratio of 280 in 50 ml of deionized water was prepared in a 400 ml beaker. The beaker was placed on a hot plate and the zeolite suspension was stirred using a magnetic stir bar. The temperature of the zeolite suspension (or slurry) was brought to around 80–85° C. A solution of dissolved alumina in phosphoric acid was also prepared by adding an amount of alumina to 10 ml of deionized water. The alumina in water was then heated and stirred until the temperature was about 70 to 80° C., at which point an amount of phosphoric acid ($H_3PO_4$) (85 wt % in aqueous) was slowly added to the slurry. A clear solution was eventually obtained indicating that all of the alumina had dissolved. The alumina/phosphoric acid solution was then added to the zeolite slurry. Heating and stirring of the slurry continued until substantially all liquids were evaporated. The zeolite was then dried at about 90° C. overnight and then was calcined in air at approximately 510° C. for 10 hrs. The modified and calcined zeolite was then crushed and sized using 20 and 40 mesh screens.

A series of catalysts A–H (see Table 1) were prepared using the above technique by varying the amount of alumina and the phosphoric acid with respect to the amount of starting $NH_4$-ZSM-5 powder. The BET surface area and total pore volume (measured by $N_2$ adsorption) for catalysts A–H are presented in Table 1 below.

Comparative Catalysts I–O

For comparison purposes, ZSM-5 zeolite catalysts were treated with phosphoric acid, but without the dissolved alumina. The starting material was an $NH_4$-ZSM-5 zeolite powder having a $SiO_2/Al_2O_3$ mole ratio of 280. For each catalyst, a slurry containing $NH_4$-ZSM-5 zeolite and 100–150 ml of deionized water was prepared in a 400 ml beaker. The beaker was placed on a hot plate and the zeolite suspension was stirred using a magnetic stir bar. The temperature of the suspension was maintained around 90° C. Phosphoric acid (85 wt % in aqueous) was added drop wise into the beaker. Heating was continued until all liquid was evaporated. The phosphoric-acid-only modified zeolite was dried at 90° C. to 110° C. for at least four hours and then was calcined at 510° C. under air for 10 hours. The calcined zeolite was then crushed and sized using 20 and 40 mesh screens.

A series of catalysts I–O (see Table 1) were prepared by varying the amount of phosphoric acid with respect to the amount of starting $NH_4$-ZSM-5 powder. BET surface area and total pore volume (measured by $N_2$ adsorption) for catalysts I–O are presented in Table 1.

Comparative Catalyst P

A non-modified ZSM-5 zeolite catalyst (Catalyst P) was also tested. The starting material was an $NH_4$-ZSM-5 zeolite powder having a $SiO_2/Al_2O_3$ mole ratio of 280. The zeolite powder was calcined at 530° C. under air for 10 hr and then pressed and sized using 20 and 40 mesh screens for use in reactor for toluene methylation reaction.

Example 1

The catalysts A–P, as referenced in Table 1 and prepared as described above, were used in toluene methylation reactions. The reactions were each carried out in a fixed bed, continuous flow type reactor. In each case, the catalyst used was dried by slowly raising the catalyst bed temperature (about 5° C./min) to 200° C. under hydrogen ($H_2$) flow for at least one hour. A premixed toluene and methanol feed (molar ratio 2/1) was added to the reactor at 200° C. and the catalyst bed inlet temperature was increased to about 500° C. The liquid hourly space velocity (LHSV) based on toluene/methanol feed was maintained at about 31 $hr^{-1}$ and cofeed of $H_2$ gas was fed and maintained to provide a $H_2$/(toluene+methanol) molar ratio of about 0.1. Water was added to the toluene and methanol feed and was vaporized prior to introduction to reactor. The $H_2O$/(toluene+methanol) molar ratio was about 0.65 and reactor pressure was about 20 psig. The following results were obtained, as presented in Table 1 below.

TABLE 1

| Catalyst # | $Al_2O_3$, g/g zeolite | $H_3PO_4$, g/g zeolite[a] | P, g/g zeolite[a] | SA, $m^2/g$ | PV, ml/g | % Tol Conv | % Tot Xyl Sel | % PX in TX |
|---|---|---|---|---|---|---|---|---|
| A | 0.014 | 0.110 | 0.035 | 328 | 0.192 | 26.0 | 93.4 | 84.5 |
| B | 0.007 | 0.110 | 0.035 | 305 | 0.188 | 21.4 | 93.6 | 87.8 |
| C | 0.014 | 0.167 | 0.053 | 298 | 0.181 | 18.3 | 95.6 | 93.2 |
| D | 0.022 | 0.216 | 0.068 | 268 | 0.167 | 13.2 | 94.9 | 91.9 |
|   |       |       | 0.068 | 268 | 0.167 | 13.3 | 95.3 | 93.2 |
| E | 0.014 | 0.220 | 0.070 | 224 | 0.135 | 13.1 | 96.4 | 97.3 |
|   |       |       | 0.070 | 224 | 0.135 | 15.5 | 95.5 | 94.8 |
| F | 0.022 | 0.259 | 0.082 | 213 | 0.128 | 17.0 | 95.3 | 93.8 |
| H | 0.014 | 0.220 | 0.070 | 223 | 0.135 | 17.5 | 95.1 | 91.6 |
| I | 0 | 0.076 | 0.024 | 331 | 0.208 | 28.2 | 92.9 | 80.7 |
| J | 0 | 0.139 | 0.044 | 299 | 0.182 | 27.0 | 93.4 | 86.6 |
| K | 0 | 0.278 | 0.088 | 229 | 0.159 | 22.9 | 94.9 | 92.6 |
| L | 0 | 0.278 | 0.088 | 183 | 0.138 | 19.6 | 94.2 | 92.5 |
| M | 0 | 0.545 | 0.123 | 156 | 0.113 | 18.9 | 95.3 | 91.7 |
| N | 0 | 0.390 | 0.123 | 156 | 0.113 | 18.9 | 95.3 | 91.2 |
| O | 0 | 0.390 | 0.172 | 164 | 0.120 | 17.2 | 94.0 | 89.1 |
| P | 0 | 0 | 0 | 375 | 0.244 | 33.4 | 89.3 | 30.8 |

[a]Based on total amount of PA used during preparation.

A decrease in BET surface area (SA) and total pore volume (PV) of the zeolite catalysts results from the alumina-PA modification, as shown in Table 1. The total pore volume of the modified zeolite catalyst may be from 0.10 ml/g to 0.20 ml/g, more particularly from 0.12 to 0.18 ml/g. For example, the non-modified ZSM-5 catalyst (catalyst P in table 1) has SA and PV of 375 $m^2/g$ and 0.244 ml/g, respectively. The alumina-PA modified catalysts, A–H in Table 1, have a SA and PV in the range of 223–328 $m^2/g$ and 0.135–0.192 ml/g, respectively.

The acidity of the modified and non-modified zeolite catalysts were characterized by using ammonia temperature programmed desorption ($NH_3$-TPD) techniques. This method is well known in the art. For the NH3-TPD analysis, the catalyst sample (0.2 g) was first dried at 500° C. for 3 hours under a He flow rate of 10 cc/min. The temperature was then reduced to 100° C. whereupon the catalyst was saturated with ammonia gas. After saturation with $NH_3$, the catalyst desorbed at 100° C. with He flow to desorb physisorbed $NH_3$ from the sample. $NH_3$-TPD was performed at a desorption temperature ramp of 18.4° C./min under He flow rate of 16 cc/min. The desorbed $NH_3$ and water (if any) were monitored during the $NH_3$-TPD run. The non-modified catalyst (Catalyst P in Table 1) shows an $NH_3$-TPD peak of about 450° C., showing the non-modified ZSM-5 catalyst had strong acid sites. The alumina-PA modified catalysts show a broad $NH_3$-TPD peak at about 300° C., showing the modified catalysts possess weak to medium strength acid sites. Examples of $NH_3$-TPD profiles for catalysts P, E and L are shown in FIG. 1.

Figure 2:
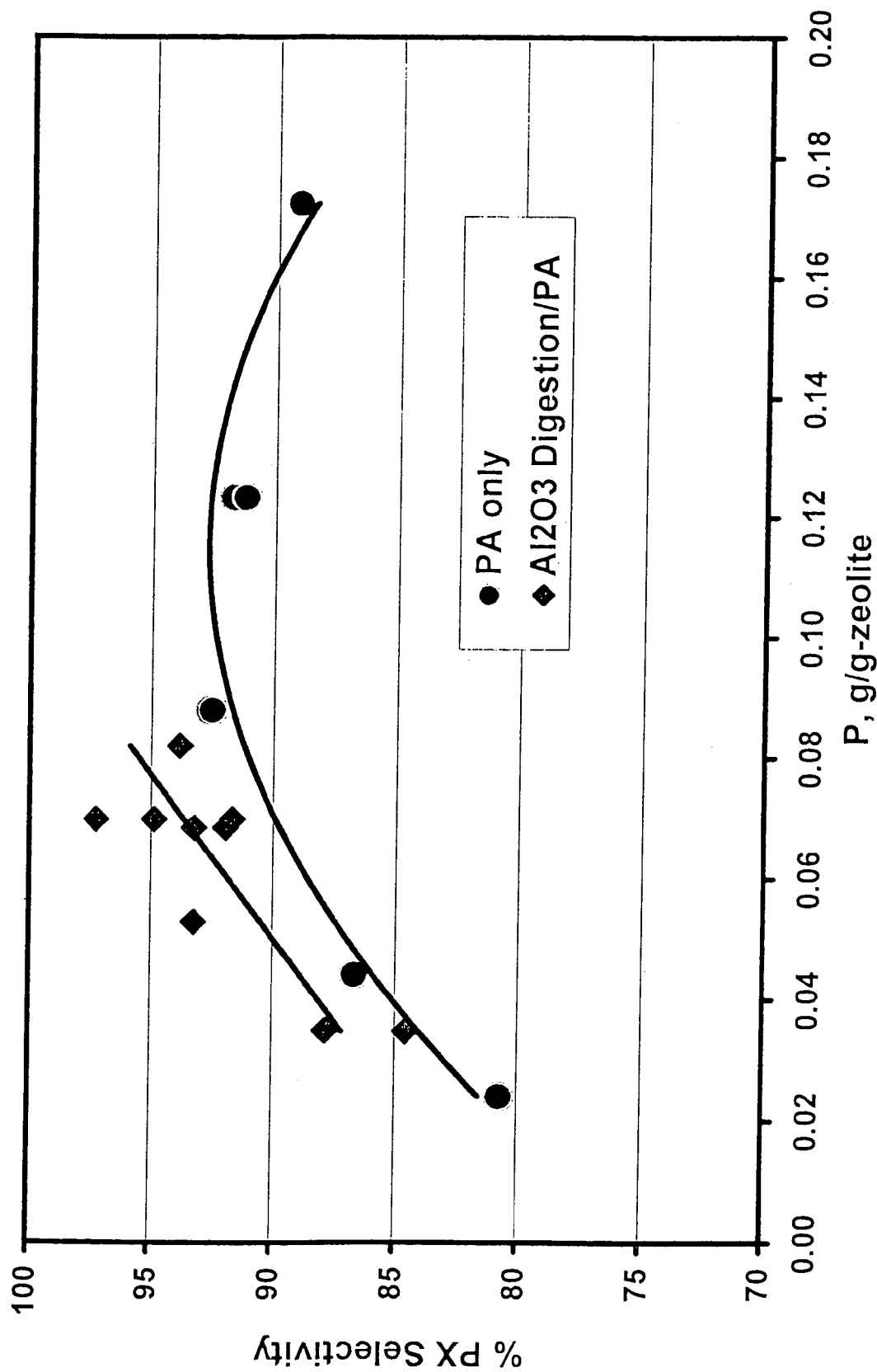
FIG. 2 is a plot of para-xylene selectivity as a function of phosphoric acid usage for zeolite catalysts treated with phosphoric acid only and those modified in accordance with the invention.

As shown in Table 1 and in FIG. 2, the alumina/phosphoric acid modified catalyst showed higher selectivity for p-xylene compared to phosphoric acid modified catalyst based upon the total amount of phosphoric acid used. The catalysts, A–E, prepared after modification by alumina-PA showed increased p-xylene selectivity with increasing PA (FIG. 1). As an example, catalyst E in Table 1 prepared by using 0.22 g $H_3PO_4$/g zeolite (0.07 g P/g zeolite) showed 95–97% p-xylene concentration in the total xylenes.

Whereas the catalysts modified by using phosphoric acid alone showed only as high as 93% p-xylene when used with 0.28 g H$_3$PO$_4$/g zeolite (0.09 g P/g zeolite).

Example 2

For comparison purposes, Catalyst E (alumina/PA-modified) and L (PA-modified) prepared using substantially the same amounts of phosphoric acid (0.22 g PA and 0.28 g PA, respectively, per gram of zeolite) were used in toluene methylation reactions. The reactions were each carried out in a fixed bed, continuous flow type reactor. In each case, the catalyst was dried by slowly raising the catalyst bed temperature (about 5° C./min) to 200° C. under hydrogen (H$_2$) flow for at least one hour. A premixed toluene and methanol feed (molar ratio 2/1) was added to the reactor at 200° C. and cofeed of H$_2$ gas was fed and maintained to provide a H$_2$/(toluene+methanol) molar ratio of about 7. Water was added to the toluene and methanol feed and was vaporized prior to introduction to reactor. The catalyst bed temperature was then increased to 500° C. A liquid hourly space velocity (LHSV) (calculated based on toluene/methanol feed only) about 2 hr$^{-1}$ was maintained. The H$_2$O/(toluene+methanol) molar ratio was about 0.7 and reactor pressure was about 20 psig. The following results were obtained and are presented in Table 2 below and FIG. 3.

TABLE 2

| Catalyst E (Alumina/PA-Modified) | | | Catalyst L (PA-Modified) | | |
|---|---|---|---|---|---|
| Run time, h | CBIT/ ° C. | % Toluene conversion | % PX selectivity | Run time, h | CBIT/ ° C. | % Toluene conversion | % PX selectivity |
| 21.8 | 498 | 16.0 | 92.3 | 4.5 | 503 | 20.1 | 90.1 |
| 45.8 | 501 | 18.8 | 92.3 | 20.3 | 506 | 21.7 | 88.6 |
| 52.3 | 502 | 20.0 | 92.2 | 43.7 | 502 | 23.6 | 89.4 |
| 116.8 | 502 | 18.2 | 92.1 | 68.2 | 502 | 23.6 | 89.6 |
| 143.1 | 503 | 18.1 | 92.0 | 74.2 | 500 | 23.3 | 89.7 |
| 167.1 | 502 | 17.9 | 91.9 | 139.7 | 501 | 22.9 | 89.7 |
| 190.8 | 502 | 18.3 | 91.8 | 146.2 | 500 | 23.2 | 89.5 |
| 220.8 | 502 | 17.8 | 91.7 | 170.2 | 501 | 22.8 | 89.6 |
| 288.3 | 503 | 17.9 | 91.7 | 194.2 | 501 | 20.2 | 89.7 |
| 315.8 | 500 | 21.6 | 91.8 | 212.2 | 529 | 21.0 | 89.8 |
| 340.3 | 504 | 17.1 | 91.8 | 242.2 | 525 | 21.0 | 88.5 |
| 364.3 | 503 | 16.7 | 91.8 | 307.7 | 525 | 20.1 | 88.0 |
| 388.3 | 501 | 17.3 | 91.8 | 314.2 | 528 | 19.6 | 87.9 |
| 453.8 | 502 | 16.8 | 91.7 | 331.7 | 526 | 19.3 | 87.6 |
| 504.3$^a$ | 501 | 13.9 | 91.5 | 338.2 | 527 | 19.6 | 87.7 |
| 526.3 | 501 | 13.8 | 91.5 | | | | |
| 549.8 | 501 | 14.7 | 91.5 | | | | |
| 622.3 | 501 | 13.9 | 91.5 | | | | |
| 628.3 | 502 | 14.3 | 91.5 | | | | |

$^a$Power outage occurred between 455 and 500 hours run time resulting in complete shutdown, and the reactor restarted.

Figure 3:
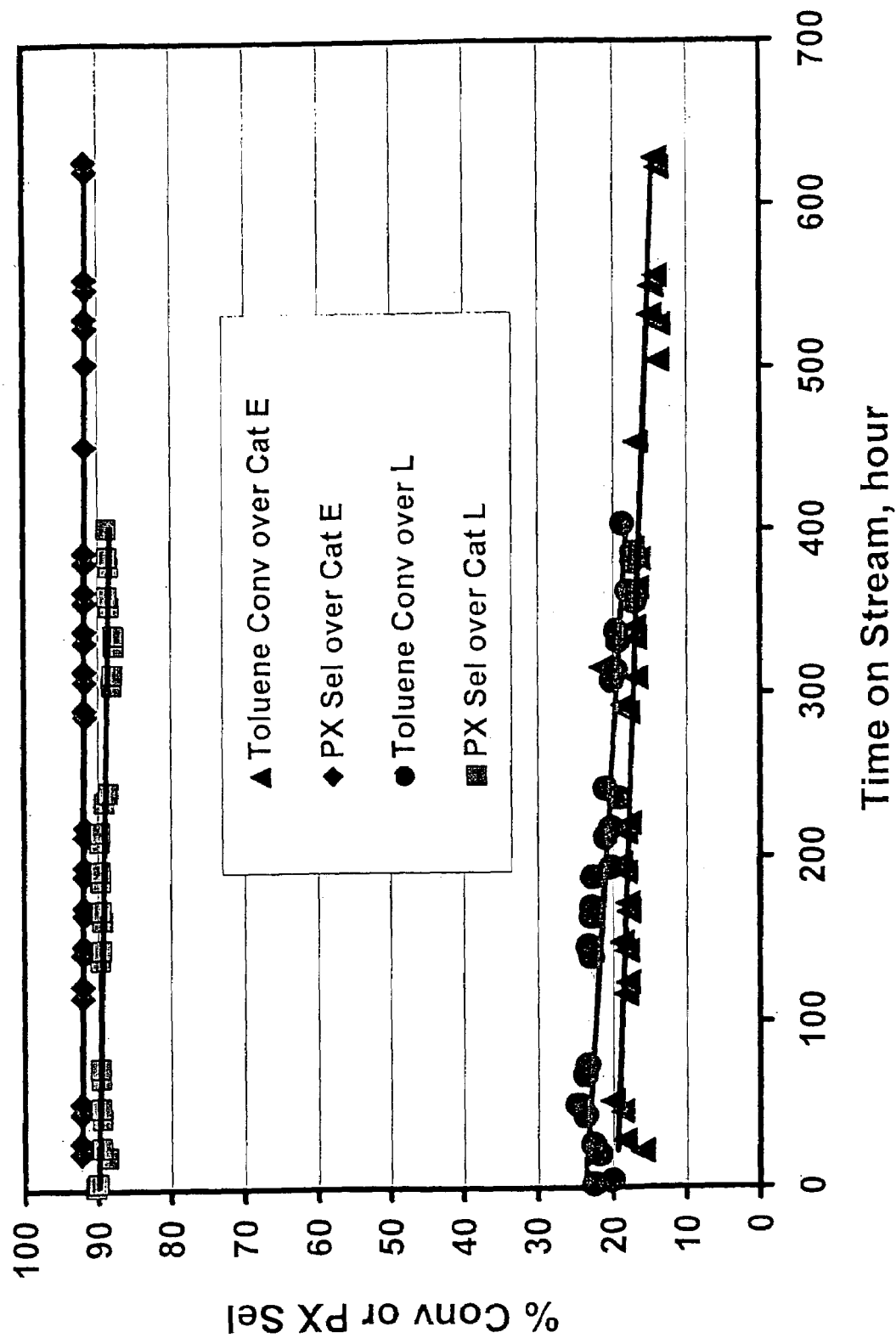
FIG. 3 is a plot of total xylene conversion and para-xylene conversion over time for catalysts treated with phosphoric acid only and that modified in accordance with the invention.

As can be seen from Table 2 and FIG. 3, the alumina/PA-modified zeolite had higher p-xylene selectivity than did the PA-only modified zeolite. Both catalysts E and L showed almost the same deactivation profiles. Catalyst E (alumina/PA-modified) showed a small decrease in toluene conversion (0.19% decrease in toluene conversion per 24 hours) at constant catalyst bed inlet temperature around 500° C. up to about 450 hour run period, at which time a power outage occurred resulting in a complete shut-down of the reactor. When the reaction was restarted the catalyst showed a lower but steady toluene conversion during 500–630 run hours. Whereas the catalyst L (PA-modified) also showed small decrease in toluene conversion (0.33% decrease in toluene conversion per 24 hours). In case of catalyst L, catalyst bed inlet temperature was around 500° C. during the first 194 hours and it was increased to about 525° C. and continued the run for about 340 hours.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing an alkyl aromatic product comprising:
    dissolving alumina in an inorganic phosphorus-containing acid;
    treating a zeolite catalyst with the alumina-containing acid solution; and
    contacting the treated zeolite catalyst with an aromatic hydrocarbon and an alkylating agent under reaction conditions suitable for aromatic alkylation.

2. The method of claim 1, wherein:
    the aromatic hydrocarbon is toluene.

3. The method of claim 2, wherein:
    the alkylating agent is methanol.

4. The method of claim 1, wherein:
    the zeolite catalyst is a ZSM-5-type zeolite catalyst.

5. The method of claim 1, wherein:
    the alumina is incorporated into the zeolite in an amount at least 0.01 gram alumina per gram of zeolite.

6. The method of claim 1, wherein:
    the modified catalyst has from about 0.03 to about 0.08 gram of phosphorus per gram of zeolite.

7. A method of preparing a xylene product comprising:
    dissolving alumina in a phosphoric acid solution;
    treating a ZSM-5-type zeolite catalyst with the alumina-containing phosphoric acid solution; and
    contacting the treated zeolite catalyst with an aromatic feed of toluene under reaction conditions suitable for at least one of toluene methylation and transalkylation.

8. The method of claim 7, wherein:
    the phosphoric acid solution used in an amount of from about 0.2 g to 0.3 g per gram of zeolite.

9. The method of claim 7, wherein:
    the alumina is incorporated into the zeolite in an amount of from about 0.01 g/g zeolite to about 0.02 g/g zeolite.

10. The method of claim 7, wherein:
    dissolving the alumina includes dissolving the alumina in an excess of phosphoric acid.

11. The method of claim 7, wherein:
    the catalyst exhibits greater than 85% para-xylene selectivity of mixed xylenes when used in toluene methylation.

12. The method of claim 7, wherein:
    the catalyst exhibits a toluene conversion over a period greater than 500 hours with a loss of conversion of less than 0.5% per day at a substantially constant catalyst bed temperature.

13. The method of claim 7, wherein:
    the toluene methylation feed contains water in an amount of at least 0.1 moles per mole of toluene/methanol.

14. The method of claim 7, wherein:
    the toluene methylation feed contains hydrogen in an amount of at least 1.0 mole per mole of toluene/methanol.

15. The method of claim 7, wherein:
    the reaction conditions include a reactor pressure of at least 10 psig.

* * * * *